United States Patent [19]
Dorsey

[11] Patent Number: 5,769,859
[45] Date of Patent: Jun. 23, 1998

[54] UMBILICAL SCISSORS

[76] Inventor: William R. Dorsey, 35 Inverness Ct., Springboro, Ohio 45065

[21] Appl. No.: 629,776

[22] Filed: Apr. 9, 1996

[51] Int. Cl.⁶ .................................................. A61B 17/42
[52] U.S. Cl. ............................................ 606/119; 30/254
[58] Field of Search ............................. 30/151–155, 194, 30/195, 244, 252, 260; 606/1, 174, 119–126

[56] References Cited

U.S. PATENT DOCUMENTS

| | | |
|---|---|---|
| 4,026,294 | 5/1977 | Mattler . |
| 4,210,148 | 7/1980 | Stivala . |
| 4,428,374 | 1/1984 | Auburn . |
| 4,438,714 | 3/1984 | Smith et al. . |
| 4,572,181 | 2/1986 | Mattler . |
| 4,648,401 | 3/1987 | Mattson . |
| 4,682,598 | 7/1987 | Beraha . |
| 4,870,965 | 10/1989 | Jahanger . |
| 5,009,657 | 4/1991 | Cotey et al. . |
| 5,127,915 | 7/1992 | Mattson . |
| 5,178,624 | 1/1993 | Kyun . |
| 5,190,556 | 3/1993 | Hessel ..................................... 606/120 |
| 5,281,228 | 1/1994 | Wolfson ................................. 606/120 |
| 5,462,555 | 10/1995 | Bolanos et al. ....................... 606/120 |
| 5,517,761 | 5/1996 | Wang ....................................... 30/254 |

*Primary Examiner*—Glenn K. Dawson
*Attorney, Agent, or Firm*—Jacox, Meckstroth & Jenkins

[57] ABSTRACT

This invention relates to umbilical scissors and, more particularly, to umbilical scissors having birth-related indicia associated therewith. In this regard, the umbilical scissors may be labeled with the birth data or provided with engraved or embossed birth data or indicia in the form of a color-coded handle to indicate the gender of a baby. Further, birth data may be provided on a label, such as a gummed label or plate, which may be mounted directly to the scissors or to a container or frame in which the scissors are placed for permanent storage and/or display.

20 Claims, 3 Drawing Sheets

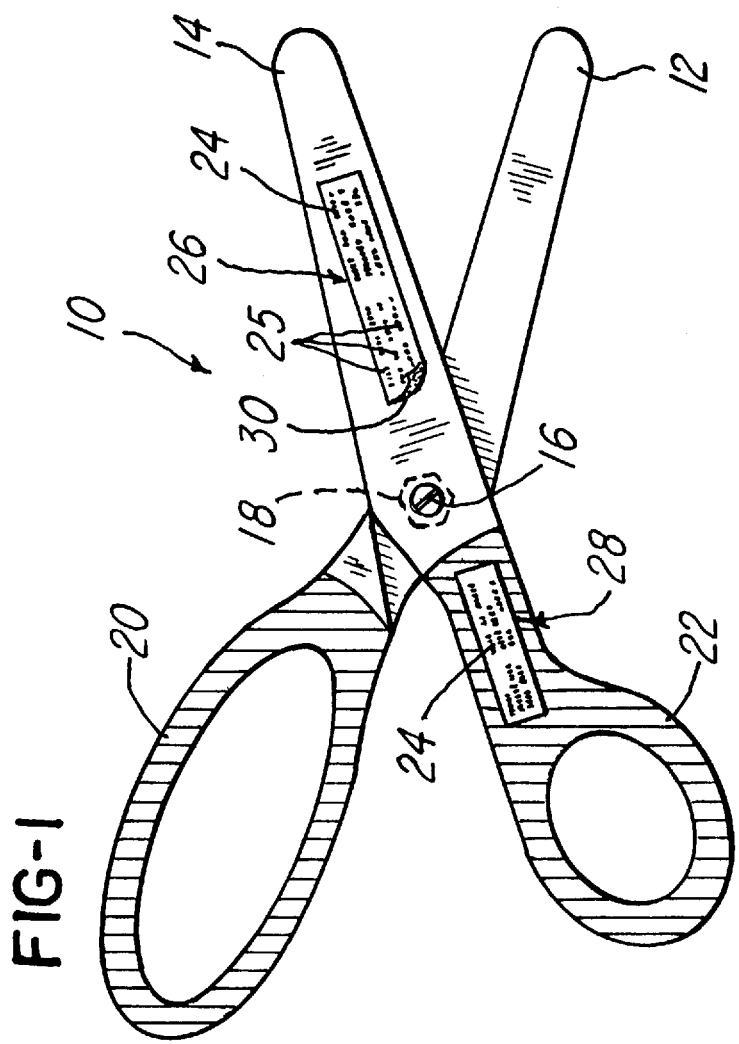

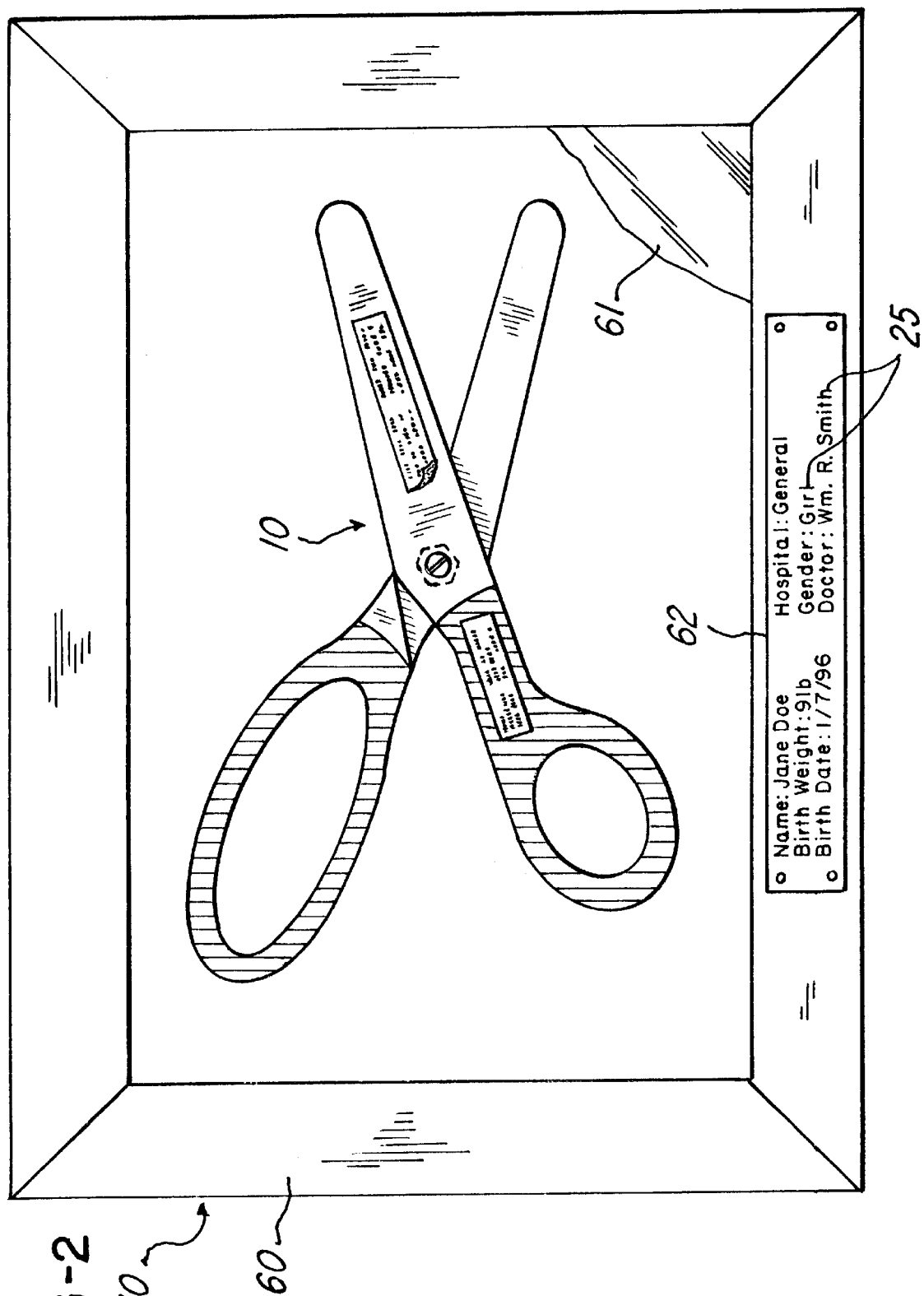

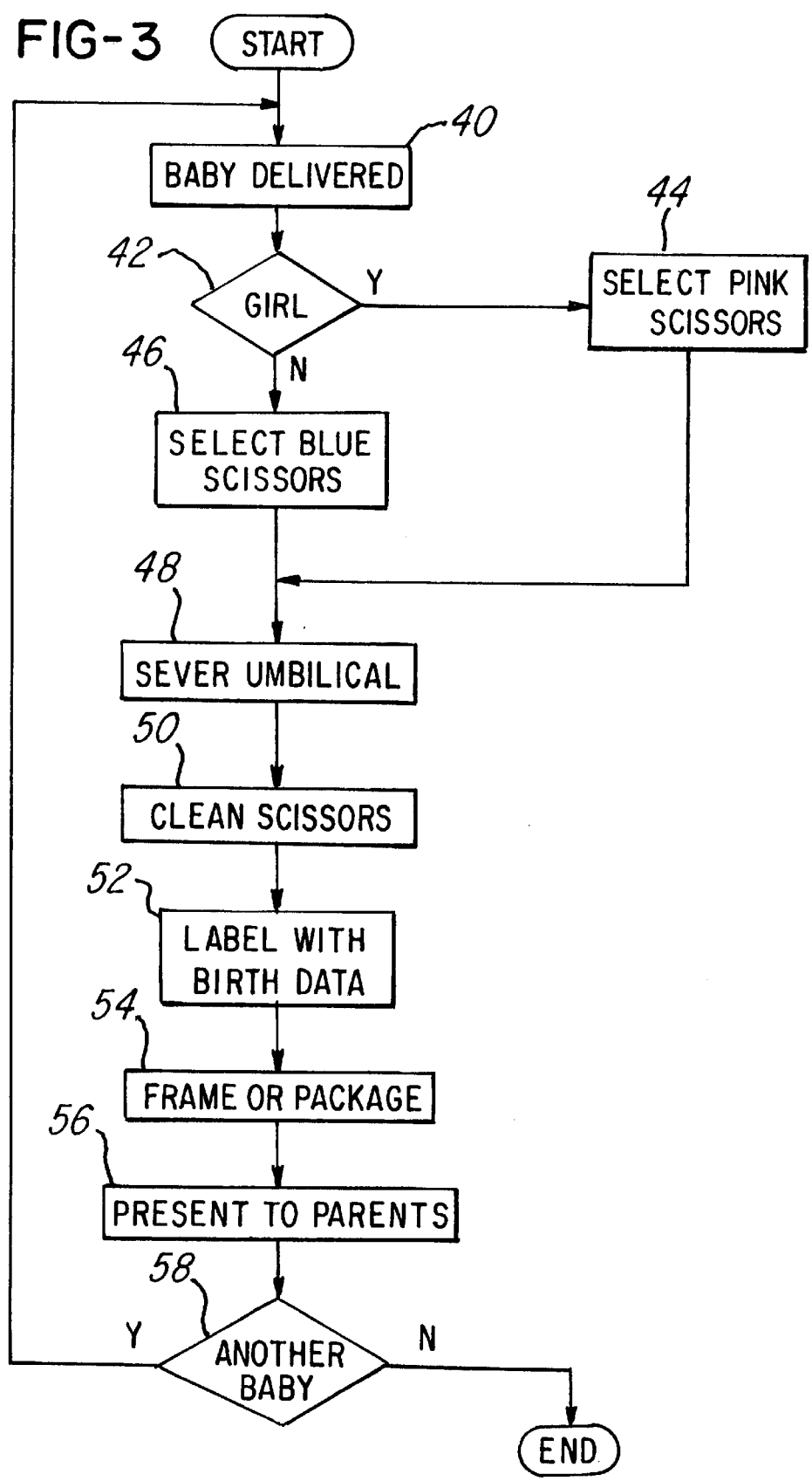

UMBILICAL SCISSORS

BACKGROUND OF THE INVENTION

1. Field of the Invention

This invention relates to umbilical scissors and, more particularly, to customized umbilical scissors having unique birth data or indicia associated therewith to facilitate memorializing and recording the birth data associated with a newborn baby.

2. Description of the Related Art

In the field of obstetrics and during a normal birthing procedure, it is necessary to sever an umbilical cord and separate a baby from its mother. Heretofore, this procedure is normally done with a pair of surgical scissors which are typically stainless steel.

In the past, no method, article or means were provided to utilize the umbilical scissors to memorialize the birthing event and as a means for recording various birthing data.

SUMMARY OF THE INVENTION

Accordingly, it is a primary object of this invention to provide a method and apparatus for memorializing or recording birth data associated with a birth of a baby utilizing umbilical scissors.

Another object of the invention is to provide umbilical scissors which have indicia associated therewith to provide an indication of a baby's gender.

It is another object of the invention to provide a pair of umbilical scissors which have a gender indicia integrally formed as a part of the handle of the scissors.

Another object of the invention is to provide birth data which may be permanently engraved or embossed, for example, on a blade of the scissors or alternatively, permanently recorded on a label which is subsequently situated or placed on the scissors.

In one aspect, this invention comprises a pair of umbilical scissors comprising a plurality of cutting edges, each of said plurality of cutting edges comprising a handle portion; a coupler for coupling said plurality of cutting edges together to enable said plurality of cutting edges to cooperate to cut an umbilical cord; an indicia associated with said plurality of cutting edges, said indicia being suitable for identifying a gender of a new born baby.

In still another aspect, this invention comprises a scissor kit comprising of a pair of scissors; and an indicia associated with said pair of scissors.

In another aspect this invention comprises a method for recording birth data comprising the steps of selecting a pair of gender-indicating scissors based on gender; severing an umbilical cord with said umbilical scissors.

These and other objects and advantages of the invention will be apparent from the following description, the accompanying drawings and the appended claims.

BRIEF DESCRIPTION OF THE DRAWINGS

FIG. 1 is a perspective view of a pair of umbilical scissors comprising features of the present invention;

FIG. 2 is a view of the umbilical scissors shown in FIG. 1 showing the scissors mounted for display in a container or frame; and FIG. 3 is a schematic diagram of a process according to an embodiment of the present invention.

DETAILED DESCRIPTION OF THE INVENTION

Referring now to FIG. 1, a pair of gender-indicating umbilical scissors 10 are shown. The scissors 10 comprise a first blade or cutting edge 12 and a second blade or cutting edge 14 which are fastened together by a suitable fastener, such as a screw 16 which cooperates with a mating bolt 18 to pivotally secure the first blade 12 to the second blade 14.

In the embodiment being described, the first blade 12 comprises a first handle 20 and the second blade 14 comprises a second handle 22. While the blades 12 and 14 are metal, the handles 20 and 22 may be completely or partially molded from a suitable rubber or plastic material as desired.

As best illustrated in FIG. 1, the scissors 10 comprise indicia 24 which may be associated with scissors 10 as shown. In the embodiment being described, the indicia 24 comprises a plurality of birth-related data 25, such as a baby's gender, name, weight, birthdate, hospital, birth time, doctor and the like. Further, the handles 20 and 22 may be integrally molded, covered, painted or the like to be colored coded to provide an indication of a baby's gender. For example, if a baby boy is delivered, the handles 20 and 22 may be covered, coated or painted blue or integrally molded with a blue material. Conversely, if the baby is a girl, the handles 20 and 22 may be covered, coated, painted or molded pink, as illustrated in FIGS. 1 and 2. Thus, it should be appreciated that while the scissors 10 in FIGS. 1 and 2 have been colored pink for illustration purposes, they could be covered, coated, painted or molded to comprise any color desired to indicate gender.

Further, if the baby to be delivered is unknown, a neutral color, such as green or yellow may be chosen. Alternatively, handle 20 may be colored blue while handle 22 is colored pink.

Although not shown, it is contemplated that a colored sheath or casing may be provided around part or all of the scissors 10 or around handles 20 and 22 to provide the color-coding and/or birth-related data indicia.

Notice that scissors 10 also comprise a plurality of label areas, such as areas 26 and 28, which may receive a label, such as a gummed label 30, which incorporates the birth data 25. Alternatively, the birth data 25 may be engraved or embossed directly into, for example, handle 22 (as shown in FIG. 1) or blade 14. As described later herein, if the birth data 25 is provided on a label, such as label 30, then it is placed on blade 14 after the scissors 10 have been used to sever the umbilical cord.

Referring now to FIG. 2, a scissor kit 70 is shown comprising a pair of scissors which are mounted for storage or display in a suitable container, such as the container defined by frame 60 and glass 61. Notice that the birth data 25 mentioned above may be situated on a label or plate 62 which, in turn, is situated on frame 60 as shown.

After the scissors 10 are mounted in frame 60, the container may be hung on a wall or otherwise placed so as to store and display the scissors 10 and birth data 25.

Thus, the scissor kit 70 provides convenient means for memorializing birth data associated with the birth of a baby and providing means for permanently recording the birth-related data 25 using the very medical instrument that was used to sever the umbilical cord and separate the baby from its mother.

Advantageously, the apparatus and method of the present invention provide convenient means and method for recording and memorializing a birthing event and the data associated with the birth of a baby. The method and apparatus also provide suitable means for memorializing the umbilical severing event during the birthing process.

It should also be appreciated that if the birth data 25 is engraved directly on, for example, blade 14 or on packaging for the scissors 10, then the need for a label 30 may be eliminated. A method for recording the birth data will now be described.

Initially, during the birthing process, a baby is delivered (block 40 in FIG. 3). At decision block 42, it is determined whether or not the baby delivered at block 40 is a girl. If it is, then a pink handled pair of scissors can be selected at block 44. If it is not, then a blue pair of scissors is selected (block 46).

At block 48, the umbilical cord (not shown) is severed using the scissors selected at either block 44 or block 46.

At block 50, the scissors 10 are cleaned and then either engraved or labeled with the birth-related data 25 mentioned above (block 52). In this regard, the gummed label 30 may be generated to have the baby's name, weight, birthdate, hospital, birth time and doctor's name. The gummed label 30 is then placed or situated at area 26 on blade 14, as illustrated in FIG. 1.

At block 54, the scissors 10 may be situated or placed in a suitable package, such as the container defined by frame 60 and glass 61 in FIG. 2. Thereafter, the scissors 10 may be given or presented to the parents at block 56.

It should be appreciated that the framing at block 54 is optional and may be skipped so that the scissors 10 may be provided to parents without frame 60, rather than provided to the parents in frame 60.

At decision block 58, it is determined if another baby is to be delivered, and if there is, then the procedure loops back to block 40 as shown. Otherwise, the procedure is complete.

The scissors 10 may then be stored or displayed with the birth data 25 permanently affixed thereto. While the methods herein described, and the forms of apparatus for carrying these methods into effect, constitute preferred embodiments of this invention, it is to be understood that the invention is not limited to these precise methods and forms of apparatus, and that changes may be made in either without departing from the scope of the invention, which is defined in the appended claims.

I claim:

1. A pair of umbilical scissors in combination with a casing comprising:

a plurality of cutting edges, each of said plurality of cutting edges comprising a handle portion;

a coupler for coupling said plurality of cutting edges together to enable said plurality of cutting edges to cooperate to cut an umbilical cord; and a casing sized and configured for housing said scissors; an indicia for identifying birth data relative to a new born baby being situated on either said casing or said scissors wherein;

said casing comprises a frame suitable for receiving and displaying said scissors.

2. A scissor kit comprising:

a pair of umbilical scissors; and a newborn indicia;

said scissor kit further comprising a container for housing said pair of scissors; said container comprising a frame for framing said pair of scissors; and said indicia being situated on either said pair of scissors or said container.

3. The scissor kit as recited in claim 2 wherein said newborn indicia comprises a gender identifier.

4. The scissor kit as recited in claim 3 wherein said newborn indicia comprises a name.

5. The scissor kit as recited in claim 3 wherein said gender identifier is integrally formed as part of said pair of scissors.

6. The scissor kit as recited in claim 2 wherein said gender identifier comprises a color.

7. The scissor kit as recited in claim 2 wherein said newborn indicia comprises a name.

8. The scissor kit as recited in claim 7 wherein said newborn indicia comprises a label situated on said pair of scissors; said label comprising birth-related data associated with a baby whose umbilical cord was severed using said pair of scissors.

9. The scissor kit as recited in claim 8 wherein said birth-related data comprises at least one of the following indicia: a name, a birth weight, a birth date, a gender.

10. The scissor kit as recited in claim 2 wherein said newborn indicia comprises a label associated with said container.

11. The scissor kit as recited in claim 2 wherein said newborn indicia comprises at least one of the following indicia: a name, a birth weight, a birth date, a gender.

12. A method for memorializing a birth of a child comprising the steps of:

providing a pair of umbilical scissors;

providing an indicia defining a plurality of birth data associated with said birth of said child; and situating said indicia on said scissors.

13. The method as recited in claim 12 wherein said method further comprises the step of:

providing said indicia on a label; and mounting the label on the pair of scissors.

14. The method as recited in claim 12 wherein said situating step further comprises the step of:

engraving said indicia on said pair of scissors.

15. The method as recited in claim 12 wherein said method further comprises the step of:

providing said pair of scissors with a color to define a gender.

16. The method as recited in claim 15 wherein said color is integrally formed in at least one handle of said pair of scissors.

17. The method as recited in claim 12 wherein said method further comprises the step of:

situating said scissors in a frame in order to display said scissors.

18. The method as recited in claim 12 wherein said birth data comprises at least one of the following: a name, a birth weight, a birth date, a gender.

19. A method of memorializing a birth of a child comprising the steps of:

providing a pair of umbilical scissors;

providing an indicia defining a plurality of birth data associated with said birth of said child; and providing a container to house said pair of scissors; and situating said indicia on either said pair of scissors or said container.

20. The method as recited in claim 19 wherein said method further comprises the steps of:

situating said birth data on a label; and placing said label on said container.

* * * * *